(12) United States Patent
Lee et al.

(10) Patent No.: US 11,370,853 B2
(45) Date of Patent: Jun. 28, 2022

(54) RESIN BEADS AND USE IN PROCESSING OF AQUEOUS SOLUTIONS

(71) Applicants: DOW GLOBAL TECHNOLOGIES LLC, Midland, MI (US); ROHM AND HAAS COMPANY, Philadelphia, PA (US)

(72) Inventors: Chang-Soo Lee, Seoul (KR); Collin H. Martin, Collegeville, PA (US); Daryl J. Gisch, Midland, MI (US); Christopher R. Eicher, Midland, MI (US)

(73) Assignees: DOW GLOBAL TECHNOLOGIES LLC; ROHM AND HAAS COMPANY

( * ) Notice: Subject to any disclaimer, the term of this patent is extended or adjusted under 35 U.S.C. 154(b) by 678 days.

(21) Appl. No.: 16/461,839

(22) PCT Filed: Dec. 30, 2016

(86) PCT No.: PCT/KR2016/015589
§ 371 (c)(1),
(2) Date: May 17, 2019

(87) PCT Pub. No.: WO2018/124349
PCT Pub. Date: Jul. 5, 2018

(65) Prior Publication Data
US 2019/0366233 A1 Dec. 5, 2019

(51) Int. Cl.
| | | |
|---|---|---|
| *B01D 15/10* | (2006.01) | |
| *B01J 20/26* | (2006.01) | |
| *B01J 20/28* | (2006.01) | |
| *B01J 20/289* | (2006.01) | |
| *C07H 1/06* | (2006.01) | |
| *C08F 8/42* | (2006.01) | |
| *C13B 20/12* | (2011.01) | |
| *B01J 20/30* | (2006.01) | |
| *B01D 15/18* | (2006.01) | |

(52) U.S. Cl.
CPC .............. *C08F 8/42* (2013.01); *B01D 15/10* (2013.01); *B01J 20/265* (2013.01); *B01J 20/28004* (2013.01); *B01J 20/289* (2013.01); *B01J 20/28016* (2013.01); *B01J 20/3085* (2013.01); *C07H 1/06* (2013.01); *C13B 20/126* (2013.01); *B01D 15/1821* (2013.01); *B01J 2220/52* (2013.01)

(58) Field of Classification Search
CPC ....... C08F 8/42; B01D 15/10; B01D 15/1821; B01J 20/265; B01J 20/28004; B01J 20/28016; B01J 20/289; B01J 20/3085; B01J 2220/52; C07H 1/06; C13B 20/126
See application file for complete search history.

(56) References Cited

U.S. PATENT DOCUMENTS

| | | | | |
|---|---|---|---|---|
| 4,565,582 A | * | 1/1986 | Filippini | ............... C13K 13/005 536/127 |
| 5,981,716 A | | 11/1999 | Zanette et al. | |
| 11,065,599 B2 | * | 7/2021 | Lee | ....................... B01J 20/3085 |
| 2010/0174059 A1 | | 7/2010 | DeFrees et al. | |

FOREIGN PATENT DOCUMENTS

| | | |
|---|---|---|
| CN | 103864858 A | 6/2014 |
| EP | 0158148 A1 | 10/1985 |
| KR | 1019980703851 A | 12/1998 |

OTHER PUBLICATIONS

European search opinion for related application 16925463. Jul. 15. (Year: 2020).*
PCT International Search Report, dated Sep. 25, 2017, for International Application PCT/KR2016/015589, filing date Dec. 30, 2016; ISA/KR, International Application Division, Korean Intellectual Property Office, 189 Cheongsa-ro, Seo-gu, Daejeon, 35208, Republic of Korea; Kim, Sun Hee, Authorized Officer.
Yurkevich, Alexander M. et al., "Study of the interaction of polyols with polymers containing N-substituted [(4-boronophenyl)methyl]-ammonio groups," Carbohydrate Research, Sep. 1975, vol. 43, No. 2, pp. 215-224 See abstract; and pp. 215-218.
Bicak, et al. "Polymer supported amino bis-(cis-propan 2,3 diol) functions for removal of trace boron from water", Reactive & Functional Polymers 65 (2005) 143-148.
Rajendran et al., "Simulated moving bed chromatography for the separation of enantiomers", in Journal of Chromatography A, vol. 1216, 2009, pp. 709-738.
Vente, J.A.et al., in "Sorption and Separation of Sugars with Adsorbents Based on Reversible Chemical Interaction," Adsorption Science and Technology, vol. 24, p. 171, 2006.
Fornstedt, et al. in Chapter 1 of Analytical Separation Sciences, (Anderson, et al., editors), published by Wiley-VCH, (2015).
Juza et al., "Simulated moving-bed chromatography and its application to chirotechnology", Trends in Biotechnology (TIBTECH) vol. 18, Mar. 2000, pp. 108-118.

* cited by examiner

*Primary Examiner* — Benjamin L Lebron

(57) ABSTRACT

A method of processing an aqueous solution,
wherein the aqueous solution comprises one or more dissolved sugar, one or more dissolved sugar alcohol, or a mixture thereof,
wherein the method comprises bringing the aqueous solution into contact with a collection of resin beads, wherein the resin beads comprise functional groups of structure (S1).

5 Claims, No Drawings

RESIN BEADS AND USE IN PROCESSING OF AQUEOUS SOLUTIONS

TECHNICAL FIELD

A common industrial goal is the processing of aqueous solutions. A category of aqueous solutions of interest are aqueous solutions that contain one or more sugar and/or one or more sugar alcohol. It is desirable to process such an aqueous solution in a way that separates some or all of the sugars and/or sugar alcohols from each other. It is also desirable to process such an aqueous solution in a way that is capable of separating some or all of the sugars and/or sugar alcohols from other compounds that may be present in the aqueous solution. It is also desirable to be able to process aqueous solutions having pH below 6.

BACKGROUND ART

In the past, aqueous solutions of sugars have been processed to separate the sugars by using resin beads that have sulfonic acid groups in calcium form. It has been found that, in order to effectively separate the sugars, such resin beads needed to be present in a collection of resin beads that had both a relatively small mean diameter and a relatively small uniformity coefficient. Production of such uniform collections of small resin beads is difficult and expensive. It is desired to provide resin beads that are capable separating sugars, even when the collection of resin beads has relatively large mean diameter and relatively large uniformity coefficient.

J. A. Vente, et al., in "Sorption and Separation of Sugars with Adsorbents Based on Reversible Chemical Interaction," *Adsorption Science and Technology*, vol. 24, p. 171, 2006, describe a boronic acid-functionalized poly(acrylamide) resin, used at pH 6 or pH 9, that is used to separate glucose and fructose. It is desired to provide resin beads of a different composition that are capable of separating a variety of sugars and sugar alcohols. It is also desired to provide resin beads that are capable of processing aqueous solutions at pH less than 6.

DISCLOSURE OF INVENTION

The following is a statement of the invention.

A first aspect of the present invention is a resin bead comprising functional groups of structure (S1)

(S1)

wherein —X— is a bivalent linking group, wherein —Y is a monovalent group having structure (S2)

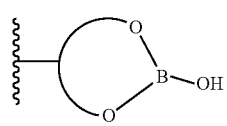
(S2)

wherein the circular structure in structure (S2) has four or more atoms,
wherein the mole ratio of multivalent atomic cations to —X— groups is either 0:1 or is 0.01:1 or lower.

A second aspect of the present invention is a method of processing an aqueous solution, wherein the aqueous solution comprises one or more dissolved sugar, one or more dissolved sugar alcohol, or a mixture thereof, wherein the method comprises bringing the aqueous solution into contact with a collection of resin beads, wherein the resin beads comprise functional groups of structure (S1)

(S1)

wherein —X— is a bivalent linking group, wherein —Y is a monovalent group having structure (S2)

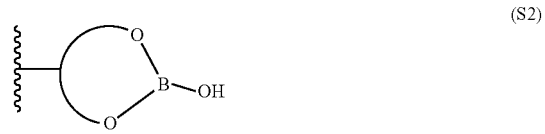
(S2)

wherein the circular structure in structure (S2) has four or more atoms.

The following is a detailed description of the invention.

As used herein, the following terms have the designated definitions, unless the context clearly indicates otherwise.

A "polymer," as used herein, is a relatively large molecule made up of the reaction products of smaller chemical repeat units. As used herein, the term "resin" is a synonym for "polymer." Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof.

Vinyl monomers have the structure (M1)

(M1)

where each of $R^1$, $R^2$, $R^3$, and $R^4$ is, independently, a hydrogen, a halogen, an aliphatic group (such as, for example, an alkyl group), a substituted aliphatic group, an aryl group, a substituted aryl group, another substituted or unsubstituted organic group, or any combination thereof. Vinyl monomers are capable of free radical polymerization to form polymers. A vinyl polymer is the product of polymerizing the double bonds of a collection of vinyl monomers.

Styrenic monomers are vinyl monomers in which each of $R^1$, $R^2$, and $R^3$ is hydrogen and —$R^4$ has the structure

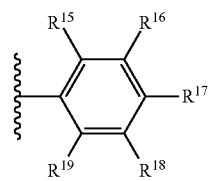

where each of $R^{15}$, $R^{16}$, $R^{17}$, $R^{18}$, and $R^{19}$ is, independently, a hydrogen, a halogen, an aliphatic group (such as, for example, an alkyl group or a vinyl group), a substituted aliphatic group, an aryl group, a substituted aryl group, another substituted or unsubstituted organic group, or any combination thereof.

Acrylic monomers are vinyl monomers in which each of —$R^1$ and —$R^2$ is hydrogen; —$R^3$ is either hydrogen or methyl; and —$R^4$ has one of the following structures:

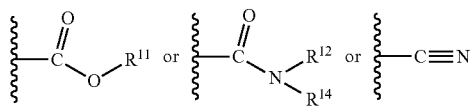

where each of $R^{11}$, $R^{12}$, and $R^{14}$ is, independently, hydrogen, a $C_1$ to $C_{14}$ alkyl group, or a substituted $C_1$ to $C_{14}$ alkyl group.

A reaction among monomers to form one or more polymers is referred to herein as a polymerization process. The residue of a monomer as part of a polymer after a polymerization process has taken place is known herein as a polymerized unit of that monomer.

As used herein, a polymer has a "backbone." To identify the backbone, a pathway is identified by starting at one end of the polymer and proceeding from one atom to the next, proceeding along covalent bonds, without any doubling back along the pathway, until another end of the polymer is reached. As used herein, an "end" of a polymer is a site of chain termination of the polymerization reaction that formed the polymer. If the polymer is branched or crosslinked, multiple such pathways are identified, connecting every end point of the polymer to every other end point of the polymer. Any atom lying upon one or more of these pathways is part of the polymer backbone. Individual atoms that are not part of any such pathway and chemical groups in which none of the atoms are part of any such pathway are known herein as "pendant". Some examples are as follows. In linear polyethylene, all the carbon atoms are in the backbone. In a linear polyamide formed by polymerization of co aminoundecanoic acid, all the carbon and nitrogen atoms are in the backbone. In a vinyl polymer, each polymerized unit is a residue of a monomer of structure (M1). The carbon atoms shown in structure (M1) form the backbone of the vinyl polymer, while —$R^1$, —$R^2$, —$R^3$, and —$R^4$ are pendant. In linear polystyrenehomopolymer, the carbon atoms from the vinyl groups of the styrene monomers form the backbone, while the aromatic rings are pendant.

In chemical structures shown herein, when a chemical group (i.e., a structure of bonded atoms that is not a complete molecule) is depicted, the point of attachment of the group to other atoms is shown herein by the symbol

For example, a hydroxyl group would be depicted herein as

and a methyl group would be depicted herein as

If the hydroxyl group and the methyl group were joined, the result would be methanol, depicted as HO—$CH_3$ or as $HOCH_3$. or as $CH_3OH$.

Resin beads are individual particles, each containing 50% or more by weight of polymer. Beads are in the solid state at 23° C. If a particle is not spherical, the diameter of the particle is taken herein to be the diameter of an imaginary sphere that has the same volume as the particle.

A collection of resin beads may be characterized by the particle diameters. The collection may be characterized by the harmonic mean diameter or by the volume-average diameter. The parameter D60 of a collection of resin beads is a diameter such that exactly 60% by volume of the beads in the collection have diameter D60 or less. The parameter D10 of a collection of resin beads is a diameter such that exactly 10% by volume of the beads in the collection have diameter D10 or less. The uniformity coefficient (UC) is the quotient UC=D60/D10. A lower UC means that the distribution of diameters is more nearly uniform (i.e., the beads are more nearly all the same diameter).

Resin beads may be characterized by their porosity. The size of the pores in a resin bead are measured by the Brunauer-Emmett-Teller (BET) method using nitrogen gas. Resin beads are said herein to be "macroporous" if the median pore diameter is 20 nm or greater. Resin beads having median pore diameter less than 20 nm, including those whose pores are too small to be detected reliably by the BET method, are said herein to be "gel" resin beads.

As used herein, a chemical group is said herein to be "substituted" if a substituent (that is, an atom or chemical group) is attached. Suitable substituents include, for example, alkyl groups, alkynyl groups, aryl groups, halogen atoms, nitrogen-containing groups including amine groups, oxygen-containing groups including carboxyl groups, sulfur-containing groups including sulfonic acid groups, nitrile groups, and combinations thereof.

As used herein, an aqueous solution is a composition that is liquid at 23° C. and that contains one or more solute compound dissolved in an aqueous solvent. A solvent is aqueous if it is liquid at room temperature and contains 50% or more water, by weight based on the weight of the solvent. A dissolved compound is considered "solid" if that compound, in the pure state, either (i) is liquid at 23° C. and has boiling point of 110° C. or higher or else (2) is solid at 23° C.

As used herein, a compound is "organic" if it contains one or more carbon atoms but does not belong to any of the following classes of compounds: binary compounds of carbon, such as carbon oxides, carbon sulfides, carbon disulfide, and similar compounds; ternary compounds such as metallic cyanides, metallic carbonyls, phosgene, carbonyl sulfide, and similar compounds; and metallic carbonates and bi-carbonates, such as calcium carbonate, sodium carbonate, sodium bicarbonate, and similar compounds. A compound is "inorganic" if it is not organic.

As used herein, a monosaccharide is an aldehyde or ketone having 2 or more hydroxyl groups. A disaccharide is a compound that could be formed by joining two monosaccharides. An oligosaccharide is a compound that could be formed by joining three to five monosaccharides. A sugar is a monosaccharide, a disaccharide, or an oligosaccharide. A sugar alcohol is a compound in which all the atoms are selected from carbon, hydrogen, and oxygen; each oxygen atom is present either as part of a hydroxyl group or as part of an ether linkage between two carbon atoms; all the bonds are single covalent bonds; there are three or more carbon atoms; and there are two or more hydroxyl groups.

An atomic cation is an atom from which one or more electron has been removed. A multivalent atomic cation is an atomic cation that has a positive charge of 2 or more.

Ratios are characterized herein as follows. For example, when a ratio is said to be 3:1 or greater, that ratio may be 3:1 or 5:1 or 100:1 but may not be 2:1. To state this in a general way, when a ratio is said herein to be X:1 or greater, it is meant that the ratio is Y:1, where Y is greater than or equal to X. Similarly, for example, when a ratio is said to be 15:1 or less, that ratio may be 15:1 or 10:1 or 0.1:1 but may not be 20:1. To state this in a general way, when a ratio is said herein to be W:1 or less, it is meant that the ratio is Z:1, where Z is less than or equal to W.

The first aspect of the present invention is resin beads that have the structure (S1)

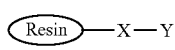
(S1)

where —X— is a bivalent linking group, wherein —Y is a monovalent group having structure (S2)

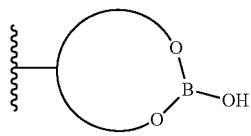
(S2)

where the circular structure in structure (S2) has four or more atoms.

In structure (S2), the group —X— is preferably bonded to a carbon atom that is part of the backbone of a polymer within the resin bead. Preferably, —X— has the structure (S10)

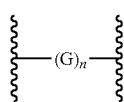
(S10)

where G is a chemical group and n is 1 or more. Preferably, n is 2 or more; more preferably 4 or more; more preferably 6 or more. Preferably n is 14 or fewer; more preferably 12 or fewer; more preferably 10 or fewer; more preferably 8 or fewer. Structure (S10) shows that one or more -G- groups are connected in a line. When n is greater than 1, all of the -G- groups may be the same as each other, or some of the -G- groups may be different from each other while some of the -G- groups are the same as each other, or there may be n different -G- groups. Preferred -G- groups are selected from (S11), (S12), (S13), and (S14):

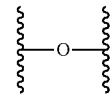
(S11)

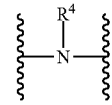
(S12)

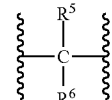
(S13)

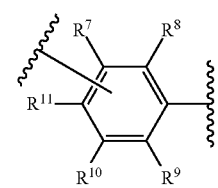
(S14)

Each of —$R^4$, —$R^5$, and —$R^6$ is, independently of each other, hydrogen, hydroxyl, amino, N-substituted amino, unsubstituted alkyl, or substituted alkyl. Each of —$R^7$, —$R^8$, —$R^9$, —$R^{10}$, or —$R^{11}$ is, independently of each other, hydrogen, hydroxyl, amino, N-substituted amino, unsubstituted alkyl, or substituted alkyl, with the proviso that one of —$R^7$, —$R^8$, —$R^9$, —$R^{10}$, or —$R^{11}$ is the connection bond between (S14) and an adjacent group or the resin backbone.

Any chemical group that has structure (S10) as defined herein above and that is bonded to the backbone of the polymer is considered herein to be an —X— group, whether or not it is bonded to a —Y group.

Preferably, —$R^4$ is unsubstituted alkyl. Preferably, —$R^4$ has 1 to 8 carbon atoms; more preferably 1 to 4 carbon atoms; more preferably 1 or 2 carbon atoms; more preferably 1 carbon atom. If more than one (S12) is present, the plural —$R^4$ groups may be chosen independently of each other. Preferably, —$R^5$ is hydrogen, hydroxyl, or unsubstituted alkyl; more preferably hydroxyl. Preferably, —$R^6$ is hydrogen, hydroxyl, or unsubstituted alkyl; more preferably hydrogen or hydroxyl. If more than one (S13) is present, the plural —$R^5$ groups may be chosen independently of each other. If more than one (S13) is present, the plural —$R^6$ groups may be chosen independently of each other.

Preferably, one or more of —$R^7$, —$R^8$, —$R^9$, —$R^{10}$, and —$R^{11}$ is hydrogen, hydroxyl, or unsubstituted alkyl. More preferably all of —$R^7$, —$R^8$, —$R^9$, —$R^{10}$, and —$R^{11}$, except for the one that is the connection bond to an adjacent group or to the resin backbone, are hydrogen, hydroxyl, or unsubstituted alkyl. More preferably all —$R^7$, —$R^8$, —$R^9$, —$R^{10}$, and —$R^{11}$, except for the one that is the connection bond to an adjacent group or to the resin backbone, are hydrogen.

Preferably, —X— has no (S11) groups. Preferably, the number of (S12) groups in —X— is 3 or fewer; more preferably 2 or fewer; more preferably 1. Preferably the number of (S13) groups in —X— is 1 or more; more preferably 2 or more; more preferably 3 or more; more preferably 4 or more; more preferably 5 or more. Preferably the number of (S13) groups in —X— is 10 or fewer; more preferably 8 or fewer; more preferably 7 or fewer; more preferably 6 or fewer; more preferably 5 or fewer. Preferably, in —X—, one or more (S13) group is present in which —R⁵ is hydroxyl and —R⁶ is hydrogen. Preferably, in —X—, one or more (S13) group is present in which —R⁵ is hydrogen and —R⁶ is also hydrogen.

A preferred —X— group has structure (S15)

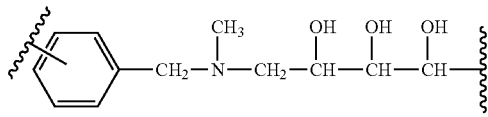
(S15)

Preferably, —Y has the structure (S16)

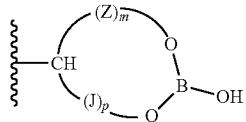
(S16)

where m is 1 or greater and p is 0 or greater. Each —Z— group and each -J- group is a bivalent chemical group, selected independently of each other. Preferably, each —Z— group and each -J- group is selected from (S11), (S12), and (S13) as defined above, where, in each —Z— group and each -J- group, each of —R⁴, —R⁵, and —R⁶ is, independently of each other, hydrogen, hydroxyl, amino, N-substituted amino, unsubstituted alkyl, or substituted alkyl.

Preferably, p is 3 or fewer; more preferably 2 or fewer; more preferably 1 or fewer; more preferably 0. Preferably, m is 1 or more. Preferably, m is 5 or fewer; more preferably 4 or fewer; more preferably 2 or fewer; more preferably 1.

Preferably, —Y is selected from structures (S3), (S4), and (S5):

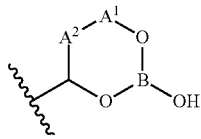
(S3)

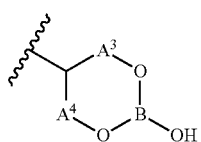
(S4)

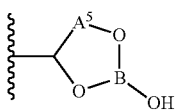
(S5)

where each of -A¹, -A²-, -A³-, -A⁴-, and -A⁵- is independently selected from structures (S6), (S7), and (S8):

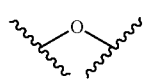
(S6)

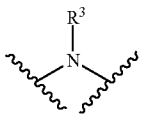
(S7)

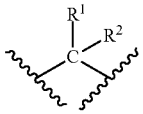
(S8)

where each of —R¹ and —R² is independently selected from hydrogen, hydroxyl, amine, unsubstituted alkyl, and substituted alkyl, and where —R³ is independently selected from hydrogen, unsubstituted alkyl, and substituted alkyl. Preferably one or more of —R¹ and —R² is hydrogen; more preferably both of —R¹ and —R² are hydrogen.

Preferably, one or more of -A¹- and -A²- is (S8); more preferably both of -A¹- and -A²- are (S8). Preferably, one or more of -A³- and -A⁴- is (S8); more preferably both of -A³- and -A⁴- are (S8). Preferably, -A⁵- is (S8).

Preferably, —Y is (S5).

The resin bead of the present invention may contain one or more "Y replacement" impurities. When a Y replacement impurity (symbolized herein as —Y^R) is present, the resin bead contains a structure (S17)

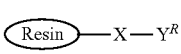
(S17)

where —Y^R is an atom, molecule, ion, or chemical group that falls outside of the definition of —Y that is given above. The bond between —X— and —Y^R may be a covalent bond or an ionic bond or a coordination bond. Some Y replacement impurities are iron chloride molecules; atomic cations of transition metals; atomic cations of zinc, cadmium, and mercury; and multivalent atomic cations of all types. Preferably, each type of Y replacement impurity is either absent or, if present, is present in a relatively small amount.

The resin bead of the present invention may contain one or more multivalent atomic cations. Preferably, multivalent atomic cations are either absent or are present in a mole ratio of multivalent atomic cations to —X— groups that is 0.01:1 or lower; more preferably 0.001:1 or lower. The resin bead of the present invention may contain one or more atomic cations of any valence value of transition elements. Preferably, atomic cations of transition elements are either absent or are present in a mole ratio of atomic cations of transition elements to —X— groups that is 0.01:1 or lower; more preferably 0.001:1 or lower.

The resin bead of the present invention may contain iron chloride. Preferably, iron chloride is either absent or is present in a mole ratio of iron chloride to —X— groups that is 0.01:1 or lower; more preferably 0.001:1 or lower. The resin bead of the present invention may contain one or more atomic cations of any valence value of elements selected from zinc, cadmium, mercury, or a mixture thereof. Preferably, atomic cations of elements selected from zinc, cadmium, mercury, or a mixture thereof are either absent or are present in a mole ratio of atomic cations of elements selected from zinc, cadmium, mercury, or a mixture thereof to —X— groups that is 0.01:1 or lower; more preferably 0.001:1 or lower.

Preferably, the mole ratio of —Y groups to —X— groups is 0.9:1 or larger; more preferably 0.95:1 or greater; more preferably 0.98:1 or greater; more preferably 0.99:1 or greater; more preferably 0.995:1 or greater. Preferably, the mole ratio of —Y groups to —X— groups is 1.001:1 or lower.

The polymer in the resin bead of the present invention may be any type of polymer, including, for example, step-reaction polymers and vinyl polymers. Step-reaction polymers include, for example, polyesters, polyamides, polyurethanes, celluloses, phenol-aldehydes, urea aldehydes, polysulfides, and polysiloxanes. Vinyl polymers include polymers having polymerized units of acrylic monomers or olefin monomers or styrenic monomers or mixtures thereof. Preferred are vinyl polymers; more preferred are vinyl polymers containing polymerized units of styrenic monomers or acrylic monomers or mixtures thereof; more preferred are vinyl polymers containing polymerized units of styrenic monomers. Among vinyl polymers, preferred are those in which the amount of polymerized units of styrenic monomers is, by weight based on the weight of the vinyl polymer, 50% or more; more preferably 75% or more; more preferably 90% or more; more preferably 95% or more.

Preferably the amount of pendant groups that contain both one or more sulfur atoms and one or more oxygen atoms is, by weight based on the weight of polymer, 0 to 0.01%; more preferably 0 to 0.003%; more preferably 0 to 0.001%; more preferably 0%. Preferably the amount of pendant groups that contain one or more sulfur atoms is, by weight based on the weight of polymer, 0 to 0.01%; more preferably 0 to 0.003%; more preferably 0 to 0.001%; more preferably 0%. Preferably the amount of pendant groups that contain both one or more carboxyl groups, either in hydrogenated form or in anionic form, is, by weight based on the weight of polymer, 0 to 0.01%; more preferably 0 to 0.003%; more preferably 0 to 0.001%; more preferably 0%. Preferably the amount of pendant groups other than —X— and —Y as defined above is, by weight based on the weight of polymer, 0 to 0.01%; more preferably 0 to 0.003%; more preferably 0 to 0.001%; more preferably 0%.

Preferably the resin beads contain polymer in an amount, by weight based on the weight of the resin beads, of 50% or more; more preferably 60% or more; more preferably 70% or more; more preferably 80% or more; more preferably 90% or more; more preferably 95% or more; more preferably 98% or more.

The resin beads of the present invention preferably are in a collection of beads that has harmonic mean particle diameter of 100 μm or higher; more preferably 200 μm or higher; more preferably 300 μm or higher; more preferably 400 μm or higher; more preferably 500 μm or higher. The resin beads of the present invention preferably are in a collection of beads that has harmonic mean particle diameter of 2000 μm or lower; more preferably 1000 μm or lower.

The resin beads of the present invention preferably are in a collection of beads that has uniformity coefficient of 1.02 or higher; more preferably 1.09 or higher; more preferably 1.16 or higher; more preferably 1.2 or higher; more preferably 1.3 or higher. The resin beads of the present invention preferably are in a collection of beads that has uniformity coefficient of 2 or lower; more preferably 1.8 or lower.

The resin beads of the present invention are preferably macroporous.

The resin beads of the present invention may be made by any method. In a preferred method, a resin is supplied having pendant groups, where the pendant group has a subgroup in which two carbon atoms are bonded to each other, and each of those two carbon atoms is also bonded to a hydroxyl group, and the subgroup is in the cis-diol configuration. The resin is then preferably put into contact with $H_3BO_3$, and the subgroup reacts with $H_3BO_3$ to form a preferred —Y group.

The second aspect of the present invention is the processing of an aqueous solution. In the practice of the second aspect of the present invention, the resin bead may or may not contain multivalent atomic cations, and if multivalent atomic cations are present, the mole ratio of multivalent atomic cations to —X— groups may or may not be 0.01:1 or lower. However, it is preferable that the amount of multivalent atomic cation is the same as the preferable amounts described above for the first aspect of the present invention.

All of the resin characteristics, including the Y replacement impurity levels, that are described above as suitable for the first aspect of the present invention are also suitable for the resin beads used in the second aspect of the present invention.

Preferably, the aqueous solution contains one or more sugars that are dissolved in the aqueous solution. Preferably, the aqueous solution contains sucrose. Preferably, the aqueous solution contains glucose. Preferably, the weight ratio of fructose to glucose is 0.1:1 or greater; more preferably 0.2:1 or greater; more preferably 0.5:1 or greater. Preferably, the weight ratio of fructose to glucose is 10:1 or lower; more preferably 5:1 or lower; more preferably 2:1 or lower.

Preferably, the aqueous solution contains one or more sugars selected from mannose, arabinose, maltose, sucrose, galactose, raffinose, stachyose, lactose, xylose, trehalose, isomaltulose, isomers thereof, versions thereof with various hydrate levels, and mixtures thereof; more preferably maltose, sucrose, raffinose, stachyose, lactose, trehalose, isomaltulose, isomers thereof, versions thereof with various hydrate levels, and mixtures thereof; more preferably maltose, sucrose, D-raffinose, stachyose, D lactose, trehalose, isomaltulose, and mixtures thereof.

Preferably, the aqueous solution contains one or more sugar alcohols that are dissolved in the aqueous solution. Preferred sugar alcohols are inositol, xylitol, maltitol, meso-erythritol, D-mannitol, sorbitol, isomers thereof, and mixtures thereof; more preferred are inositol, xylitol, D-mannitol, sorbitol, and mixtures thereof.

Preferably, the total amount of all sugars in the aqueous solution is, by weight based on the weight of the aqueous solution, 0.1% or more; more preferably 0.5% or more; more preferably 1% or more; more preferably 5% or more; more preferably 10% or more. Preferably, the total amount of all sugars in the aqueous solution is, by weight based on the weight of the aqueous solution, 70% or less; more preferably 60% or less.

Preferably, the aqueous solution has pH of less than 6; more preferably 5.5 or less; more preferably 5 or less; more preferably 4.5 or less. Preferably, the aqueous solution has pH of 2 or more; more preferably 2.5 or more.

Preferably, the total amount of all sugar alcohols in the aqueous solution is, by weight based on the weight of the aqueous solution, 0.05% or more; more preferably 0.1% or more. Preferably, the total amount of all sugar alcohols in the aqueous solution is, by weight based on the weight of the aqueous solution, 15% or less; more preferably 10% or less.

In some embodiments, the aqueous solution contains ethanol.

In some embodiments, the aqueous solution contains one or more dissolved inorganic salt. Among dissolved inorganic salts, preferred cations are sodium, potassium, and mixtures thereof; more preferably potassium. Among dissolved inorganic salts, the preferred anion is chloride. Preferably, the total amount of all dissolved inorganic salts is, by weight based on the weight of the aqueous solution, 0-10%; more preferably 0-5%.

It is contemplated that contacting the aqueous solution with the resin beads will be performed as part of a process that serves to separates some of the dissolved components from each other. Any such process of separating the components is contemplated. Two examples of such processes are pulse processes and continuous processes.

In a pulse process a fixed amount of resin beads and a fixed amount of aqueous solution are brought into contact. For example, the resin beads may be present in a container that has an inlet that allows liquid into the container and an outlet that allows liquid to exit the container, while retaining the resin beads in the container. An example of such a container is a chromatography column. For example, in a pulse process that employs a chromatography column, a fixed amount of resin beads could be placed in the column, and then a fixed amount of the aqueous solution could be placed at the top of the column in contact with the resin beads. Then, a liquid called an "eluent" could be passed through the inlet onto the top of the column, travel through the column, making contact with the resin beads, and exit through the outlet. A sufficient volume of eluent could be passed through the column until all of the desired components were removed. It is contemplated that different components will proceed through the column and out through the outlet, dissolved in the eluent, at different speeds because of different affinities for the resin beads.

In a pulse process, preferred eluents are aqueous solutions that, prior to entry into the column, do not contain any sugars or sugar alcohols. Preferred eluents are aqueous solutions of pH 3 to 11 that optionally contain one or more dissolved inorganic salts; more preferred is water of pH 3 to 11 that does not contain significant amounts of any solutes other than those necessary to establish the desired pH. The most preferred eluent is water of pH 6 to 8.

In a continuous process, fresh aqueous solution is continuously brought into contact with resin beads, and one or more product stream is removed from the resin beads. A preferred continuous process is a simulated moving bed (SMB) process. SMB processes are explained, for example, by Juza et al. in *Trends in Biotechnology (TIBTECH)* volume 18, March 2000, pp 108-118, and by Rajendran et al. in *Journal of Chromatography A*, volume 1216, 2009, pp 709-738. The eluents (also called "desorbents" in SMB processes) preferred for use in an SMB process are the same as those discussed above for a pulse process.

In some embodiments, a pulse process is performed as a test in order to determine the feasibility of a continuous process. For example, an aqueous solution of compound "A" may be processed in a pulse process using water as eluent, and the retention time (that is, the time needed for "A" to leave the column) is noted. Then, a separate pulse process may be performed on an aqueous solution of compound "B" also using water as an eluent, under the same conditions, and the retention time of "B" is noted. If the retention times for "A" and "B" are sufficiently different, it is contemplated that a solution that contained both "A" and "B" could be separated into separate solutions, one containing "A" and the other containing "B," by using an SMB process.

To determine if the retention times for "A" and "B" are sufficiently different, the resolution is studied. Resolution is defined, for example, by Fornstedt, et al. in Chapter 1 of *Analytical Separation Sciences*, (Anderson, et al., editors), published by Wiley-VCH, 2015). In the pulse process for "A," the concentration of "A" in the exit stream from the column is studied as a function of time, with time equal to zero at the moment the eluent flow is begun. The concentration versus time forms a peak, which is modeled as a triangle. The time value at the apex of the triangle is the retention time ($t_A$), and the peak width ($W_A$) is the width of the triangle at the baseline. The pulse process for "B" determines the retention time ($t_B$), and the peak width ($W_B$) characteristic of "B". When "B" is the compound with higher retention time, the resolution $R_{AB}$ is then $$R_{AB}=2(t_B-t_A)/(W_A+W_B)$$

Higher resolution means that the pair of "A" and "B" could be more readily separated.

The following are examples of the present invention.

EXAMPLE 1: PREPARATION OF RESIN BEADS

Resin beads DOWEX™ BSR-1 were used. These beads are macroporous, contain styrene/divinylbenzene copolymer, and contain pendant groups of the structure (S18):

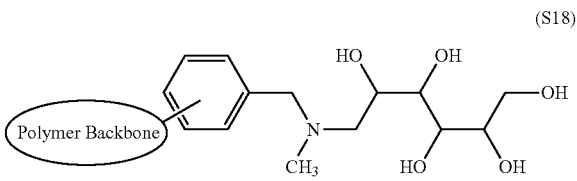

where the symbol

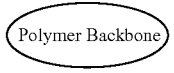

represents the polymer backbone. The two carbon atoms at the far right hand side of (S18) and their attached hydroxyl groups are in a cis-diol configuration. To make the resin beads of the present invention, 1.5 L of DOWEX™ BSR-1 beads was mixed with 2 L of a 2.0 N solution of $H_3BO_3$ in deionized water. The mixture was stirred for 2 hours at room temperature (approximately 23° C.). Then excess liquid was decanted, and the resin was rinsed with deionized water until the pH of the rinse water was approximately 7. It is contemplated that the pendant groups shown above were all converted to the following structure (S19):

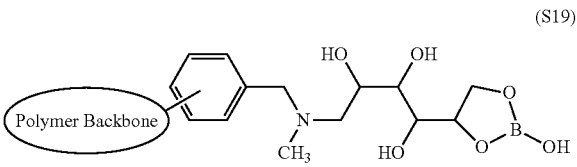

The collection of resin beads produced in Example 1 had harmonic mean diameter of 611 μm and had uniformity coefficient of 1.39.

EXAMPLE 2: PULSE TESTS ON VARIOUS SOLUTES

Pulse tests were performed on the following solutes:

TABLE 1

List of Solutes

| Label | Solute |
|---|---|
| A | Inositol |
| B | Xylitol |
| C | D-Mannose |
| D | Glucose |
| E | Maltitol |
| F | L-Arabinose |
| G | Maltose |
| H | Sucrose |
| I | Meso-Erythritol |
| J | D-Galactose |
| K | D-Raffinose (Pentahydrate) |
| L | Stachyose |
| M | D-Mannitol |
| N | D-Lactose (Monohydrate) |
| O | D-Xylose |
| P | Sorbitol |
| Q | Fructose |
| S | Potassium Chloride |
| T | Trehalose |
| U | Isomaltulose |

Pulse tests were performed as follows. A solution of a single solute was prepared at 20% by weight solute in water. A column was used that was 91 cm tall and 2.7 cm diameter. Volume of resin packed in the column was 526 mL. 26.3 mL of the solution was placed on top of the resin in the column. Elution was performed with water at 2.0 column volumes per hour (17.47 mL/min) at 60° C. "Comparative" ("Com") tests were performed using DOWEX® BSR-1 resin, and "Example" ("Ex") tests were performed using resin made by the method of Example 1.

For each pulse test, a retention time and a width was determined. Then, for a given resin type and a given pair of solutes, a resolution was determined using resolution calculation as defined by Fornstedt et al., as described above. The resolution values were as follows:

TABLE 2A

Resolution Values for Solute Pairs

|   | A Com | A Ex | B Com | B Ex | C Com | C Ex | D Com | D Ex |
|---|---|---|---|---|---|---|---|---|
| B | 0.032 | 0.260 | | | | | | |
| C | 0.040 | 0.064 | 0.009 | 0.200 | | | | |
| D | 0.008 | 0.023 | 0.023 | 0.274 | 0.032 | 0.085 | | |
| E | 0.044 | 0.061 | 0.074 | 0.187 | 0.081 | 0.002 | 0.051 | 0.081 |
| F | 0.063 | 0.098 | 0.031 | 0.170 | 0.022 | 0.034 | 0.054 | 0.118 |
| G | 0.035 | 0.027 | 0.065 | 0.277 | 0.073 | 0.089 | 0.042 | 0.004 |
| H | 0.043 | 0.025 | 0.074 | 0.268 | 0.081 | 0.085 | 0.051 | 0.003 |
| I | 0.058 | 0.087 | 0.026 | 0.174 | 0.017 | 0.025 | 0.050 | 0.107 |
| J | 0.027 | 0.068 | 0.004 | 0.184 | 0.012 | 0.008 | 0.019 | 0.088 |
| K | 0.077 | 0.065 | 0.107 | 0.283 | 0.114 | 0.118 | 0.084 | 0.044 |
| L | 0.149 | 0.087 | 0.181 | 0.345 | 0.188 | 0.151 | 0.157 | 0.060 |

As an illustration of how data are presented in the table above, the following is noted. For solutes J and B, resolution in the comparative resin was 0.004, while resolution in the Example resin was 0.184.

TABLE 2B

Resolution Values for Solute Pairs

|   | E Com | E Ex | F Com | F Ex | G Com | G Ex | H Com | H Ex |
|---|---|---|---|---|---|---|---|---|
| F | 0.104 | 0.030 | | | | | | |
| G | 0.008 | 0.084 | 0.095 | 0.122 | | | | |
| H | 0.001 | 0.081 | 0.104 | 0.117 | 0.008 | 0.001 | | |
| I | 0.100 | 0.022 | 0.005 | 0.008 | 0.091 | 0.111 | 0.100 | 0.107 |
| J | 0.069 | 0.006 | 0.034 | 0.024 | 0.060 | 0.092 | 0.069 | 0.088 |
| K | 0.033 | 0.113 | 0.136 | 0.148 | 0.041 | 0.040 | 0.034 | 0.040 |
| L | 0.098 | 0.142 | 0.214 | 0.188 | 0.107 | 0.055 | 0.100 | 0.055 |

TABLE 2C

Resolution Values for Solute Pairs

|   | I Com | I Ex | J Com | J Ex | K Com | K Ex |
|---|---|---|---|---|---|---|
| J | 0.029 | 0.016 | | | | |
| K | 0.133 | 0.137 | 0.101 | 0.120 | | |
| L | 0.211 | 0.174 | 0.173 | 0.152 | 0.061 | 0.006 |

TABLE 2D

Resolution Values for Solute Pairs

|   | E Com | E Ex | F Com | F Ex | G Com | G Ex | H Com | H Ex |
|---|---|---|---|---|---|---|---|---|
| F | 0.104 | 0.030 | | | | | | |
| G | 0.008 | 0.084 | 0.095 | 0.122 | | | | |
| H | 0.001 | 0.081 | 0.104 | 0.117 | 0.008 | 0.001 | | |
| I | 0.100 | 0.022 | 0.005 | 0.008 | 0.091 | 0.111 | 0.100 | 0.107 |
| J | 0.069 | 0.006 | 0.034 | 0.024 | 0.060 | 0.092 | 0.069 | 0.088 |
| K | 0.033 | 0.113 | 0.136 | 0.148 | 0.041 | 0.040 | 0.034 | 0.040 |
| L | 0.098 | 0.142 | 0.214 | 0.188 | 0.107 | 0.055 | 0.100 | 0.055 |

TABLE 2E

Resolution Values for Solute Pairs

|   | A Com | A Ex | B Com | B Ex | C Com | C Ex | D Com | D Ex |
|---|---|---|---|---|---|---|---|---|
| M | 0.021 | 0.224 | 0.010 | 0.025 | 0.018 | 0.167 | 0.013 | 0.239 |
| N | 0.051 | 0.040 | 0.081 | 0.293 | 0.089 | 0.103 | 0.059 | 0.016 |
| O | 0.080 | 0.189 | 0.049 | 0.060 | 0.040 | 0.131 | 0.071 | 0.205 |
| P | 0.016 | 0.334 | 0.015 | 0.096 | 0.023 | 0.280 | 0.008 | 0.345 |
| Q | 0.040 | 0.285 | 0.009 | 0.026 | 0.000 | 0.225 | 0.032 | 0.298 |
| S | 0.015 | 0.133 | 0.022 | 0.160 | 0.031 | 0.062 | 0.006 | 0.154 |
| T | 0.035 | 0.032 | 0.065 | 0.284 | 0.073 | 0.094 | 0.043 | 0.008 |
| U | 0.046 | 0.352 | 0.076 | 0.146 | 0.083 | 0.307 | 0.053 | 0.361 |

TABLE 2F

Resolution Values for Solute Pairs

|   | E Com | E Ex | F Com | F Ex | G Com | G Ex | H Com | H Ex |
|---|---|---|---|---|---|---|---|---|
| M | 0.063 | 0.156 | 0.040 | 0.138 | 0.055 | 0.242 | 0.063 | 0.235 |
| N | 0.008 | 0.097 | 0.111 | 0.137 | 0.016 | 0.012 | 0.009 | 0.013 |
| O | 0.119 | 0.122 | 0.019 | 0.102 | 0.111 | 0.208 | 0.120 | 0.201 |
| P | 0.058 | 0.264 | 0.045 | 0.255 | 0.049 | 0.347 | 0.058 | 0.338 |
| Q | 0.081 | 0.211 | 0.021 | 0.197 | 0.072 | 0.301 | 0.081 | 0.292 |
| S | 0.065 | 0.056 | 0.058 | 0.026 | 0.055 | 0.158 | 0.065 | 0.151 |
| T | 0.008 | 0.089 | 0.095 | 0.128 | 0.000 | 0.004 | 0.007 | 0.005 |
| U | 0.002 | 0.292 | 0.106 | 0.285 | 0.010 | 0.363 | 0.002 | 0.355 |

TABLE 2G

Resolution Values for Solute Pairs

|   | I Com | I Ex | J Com | J Ex | K Com | K Ex | L Com | L Ex |
|---|-------|------|-------|------|-------|------|-------|------|
| M | 0.035 | 0.142 | 0.006 | 0.153 | 0.096 | 0.252 | 0.168 | 0.306 |
| N | 0.107 | 0.125 | 0.076 | 0.106 | 0.025 | 0.030 | 0.089 | 0.044 |
| O | 0.024 | 0.107 | 0.051 | 0.118 | 0.151 | 0.221 | 0.228 | 0.271 |
| P | 0.041 | 0.256 | 0.011 | 0.263 | 0.091 | 0.346 | 0.162 | 0.410 |
| Q | 0.016 | 0.199 | 0.012 | 0.209 | 0.112 | 0.304 | 0.185 | 0.369 |
| S | 0.052 | 0.034 | 0.017 | 0.050 | 0.104 | 0.181 | 0.192 | 0.232 |
| T | 0.091 | 0.116 | 0.060 | 0.097 | 0.041 | 0.037 | 0.106 | 0.052 |
| U | 0.102 | 0.286 | 0.071 | 0.361 | 0.032 | 0.361 | 0.097 | 0.417 |

TABLE 2H

Resolution Values for Solute Pairs

|   | M Com | M Ex | N Com | N Ex | O Com | O Ex | P Com | P Ex |
|---|-------|------|-------|------|-------|------|-------|------|
| N | 0.071 | 0.257 |       |       |       |       |       |       |
| O | 0.057 | 0.034 | 0.127 | 0.223 |       |       |       |       |
| P | 0.005 | 0.116 | 0.066 | 0.363 | 0.063 | 0.149 |       |       |
| Q | 0.018 | 0.050 | 0.088 | 0.317 | 0.039 | 0.086 | 0.023 | 0.071 |
| S | 0.010 | 0.126 | 0.074 | 0.175 | 0.078 | 0.087 | 0.004 | 0.251 |
| T | 0.055 | 0.248 | 0.016 | 0.008 | 0.111 | 0.214 | 0.050 | 0.354 |
| U | 0.065 | 0.163 | 0.006 | 0.377 | 0.122 | 0.191 | 0.060 | 0.058 |

TABLE 2I

Resolution Values for Solute Pairs

|   | Q Com | Q Ex | S Com | S Ex | T Com | T Ex |
|---|-------|------|-------|------|-------|------|
| S | 0.031 | 0.189 |       |       |       |       |
| T | 0.072 | 0.308 | 0.055 | 0.165 |       |       |
| U | 0.083 | 0.124 | 0.068 | 0.284 | 0.010 | 3.465 |

Use of the Example resin brings about a general improvement in the resolution values. For example, for a specific pair of solutes, one can consider the quotient of the resolution values RQ=(resolution using Ex resin)/(resolution using Comresin).

One aspect of the general improvement becomes apparent if the results are ignored for pairs where the resolution is low for both the Com resin and the Ex resin. For example, in one analysis, the data are ignored if, for a specific pair of solutes, the resolution using Com resin and the resolution using Ex resin are both below 0.16. In this analysis, both resins are poor at resolution for that specific pair of solutes, and so it is irrelevant which one is better. In the remaining data (that is, when all the solute pairs are considered in which one resolution or the other, or both, is 0.16 or above, the quotient RQ varies from 0.81 (solute pair CL) to 659 (solute pair CQ). Thus, whenever at least one resin has a resolution of 0.16 or higher, either the resins are similar or else the Example resin is better, possibly far better.

In another analysis, pairs are considered in which results are ignored for solute pairs in which the resolution using the Comparative resin and the resolution using the Example resin are both below 0.22. Then the quotient RQ varies from 1.19 (solute pair LO) to 659 (solute pair CQ). Thus, in any solute pair in which at least one resin shows relatively good resolution (that is, 0.22 or above), the Example resin is always better. A few representative RQ values from this data set are shown below:

| Solute Pair: | AM | AP | BC | BD | BJ | CP | CQ | DM | DP |
|---|---|---|---|---|---|---|---|---|---|
| RQ: | 10 | 21 | 23 | 12 | 52 | 12 | 659 | 18 | 43 |

| Solute Pair: | EU | HU | IQ | JP | JQ | KU | NU | PS | TU |
|---|---|---|---|---|---|---|---|---|---|
| RQ: | 179 | 143 | 12 | 24 | 17 | 11 | 62 | 70 | 361 |

EXAMPLE 3: SEPARATION OF MIXED-SUGAR SOLUTION

The following Comparative Resins were tested:
CR-2=Macroporous resin similar to the resin of Example 1, having the same harmonic mean diameter (611 μm) and the same uniformity coefficient (1.39). However, the pendant groups, instead of (S19), were (S20):

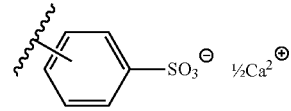

(S20)

CR-3=Macroporous resin similar to CR-2, but harmonic mean diameter of 640 μm and uniformity coefficient of less than 1.1.
CR-4=Resin similar to CR-2, but was a gel resin, had harmonic mean diameter of 320 μm and had uniformity coefficient of less than 1.1.
CR-5=DOWEX™ BSR-1. This resin is similar to Example 1 except for having pendant groups (S18) instead of pendant groups (S19).

An aqueous sugar solution was prepared that contained 42% by weight fructose, that also contained glucose, and that had 50.05% dissolved solids by weight. Sugar concentration was 50 Brix.

Resin was placed in a column as in Example 2. A sample of the aqueous sugar solution was placed onto the top of the column. The volume of aqueous sugar solution was 11.2% of the column volume. The column was then eluted with water at 1.2 bed volume per hour at 60° C. The column had 25 mm diameter and 1219 mm length. Total bed volume was 525 mL. Individual fractions of eluate were collected with an autosampler. Each fraction was analyzed for the presence and type of sugar using high performance liquid chromatography (HPLC) using AMINEX™ HPX-87C column (Bio-Rad Laboratories, Inc.) at 85° C., 0.6 mL/min, 20 μL injection volume. The concentration results for glucose and fructose from the fractions were plotted against the elution volume (bed volumes) and the resolution calculated using the methods described above. As in Example 2, a resolution value for glucose and fructose was obtained. The experiment was performed four times, using four different resins, with results as follows:

| Resin | Size[1] | UC[2] | Pendant | Type[3] | Resolution |
|---|---|---|---|---|---|
| Example 1 | 611 μm | 1.39 | S19 | M | 0.37 |
| CR-2 | 611 μm | 1.39 | S20 | M | 0.16 |

-continued

| Resin | Size[1] | UC[2] | Pendant | Type[3] | Resolution |
|---|---|---|---|---|---|
| CR-3 | 640 μm | <1.1 | S20 | M | 0.19 |
| CR-4 | 320 μm | <1.1 | S20 | gel | 0.32 |
| CR-5 | 611 μm | 1.39 | S18 | M | 0.01 |

[1]Harmonic Mean Diameter
[2]Uniformity Coefficient
[3]M = macroporous

The table shows that, when using sulfonate pendant groups (i.e., S20), the only resin having resolution value above 0.3 was CR-4, which had both small diameter and uniform distribution. The Example 1 resin (using the Boron-containing pendant group S19) achieved the best resolution value even though it has relatively large size and relatively large uniformity coefficient. Also, comparison of Example 1 with CR-5 shows that the presence of the boron-containing group greatly improves the resolution.

The invention claimed is:

1. A method of processing an aqueous solution,
   wherein the aqueous solution comprises one or more dissolved sugar,
   one or more dissolved sugar alcohol, or a mixture thereof,
   wherein the method comprises bringing the aqueous solution into contact with a collection of resin beads, wherein the resin beads comprise functional groups of structure (S1)

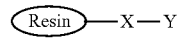
(S1)

wherein —X— is a bivalent linking group, wherein —Y is a monovalent group having structure (S2)

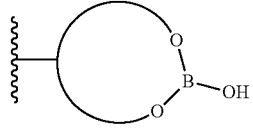
(S2)

wherein the circular structure in structure (S2) has four or more atoms.

2. The method of claim 1, wherein the aqueous solution has pH less than 6.

3. The method of claim 1, wherein the dissolved sugar is present in an amount, by weight based on the weight of the aqueous solution, of 5% to 60%.

4. The method of claim 1, wherein the collection of resin beads has harmonic mean diameter of 200 μm or higher.

5. The method of claim 1, wherein the collection of resin beads has uniformity coefficient of 1.02 or greater.

* * * * *